United States Patent [19]

Citak et al.

[11] Patent Number: 4,773,401
[45] Date of Patent: Sep. 27, 1988

[54] PHYSIOLOGIC CONTROL OF PACEMAKER RATE USING PRE-EJECTION INTERVAL AS THE CONTROLLING PARAMETER

[75] Inventors: Brian P. Citak; Michael W. Dooley, both of Minneapolis; Arthur L. Olive, Stacy; Brian D. Pederson, St. Paul; Renold J. Russie, New Brighton; Rodney W. Salo, Fridley; William L. Zimmer, Roseville, all of Minn.

[73] Assignee: Cardiac Pacemakers, Inc., St. Paul, Minn.

[21] Appl. No.: 87,869

[22] Filed: Aug. 21, 1987

[51] Int. Cl.⁴ ............................................. A61N 1/30
[52] U.S. Cl. .............................................. 128/419 PG
[58] Field of Search ................................. 128/419 PG

[56]   References Cited
   U.S. PATENT DOCUMENTS

| 4,535,774 | 8/1985 | Olson | 128/419 PG |
| 4,674,518 | 6/1987 | Salo | 128/695 |
| 4,719,921 | 1/1988 | Chirife | 128/419 PG |

Primary Examiner—William E. Kamm
Attorney, Agent, or Firm—Orrin M. Haugen; Thomas J. Nikolai; Frederick W. Niebuhr

[57] ABSTRACT

A multi-pole pacing/sensing lead is used to measure the instantaneous impedance in the right ventricle of a patient's heart. The resulting impedance waveform is signal processed to obtain a measure of the time interval beginning with the occurrence of a paced beat or a spontaneous QRS complex (systole marker) and ending with the point where the impedance versus time signal crosses the zero axis in the positive direction following the paced or spontaneous QRS complex initiating the interval or some other predetermined point along the positive-going waveform. The resulting time interval is inversely proportional to the contractility of the heart and is found to decrease with exercise and the introduction of catecholamines. Thus, it can be used as a control parameter for a demand-type cardiac pacemaker. A means for obviating changes in pacing rate due to long-term drift in the impedance sensing circuitry is also disclosed.

8 Claims, 3 Drawing Sheets

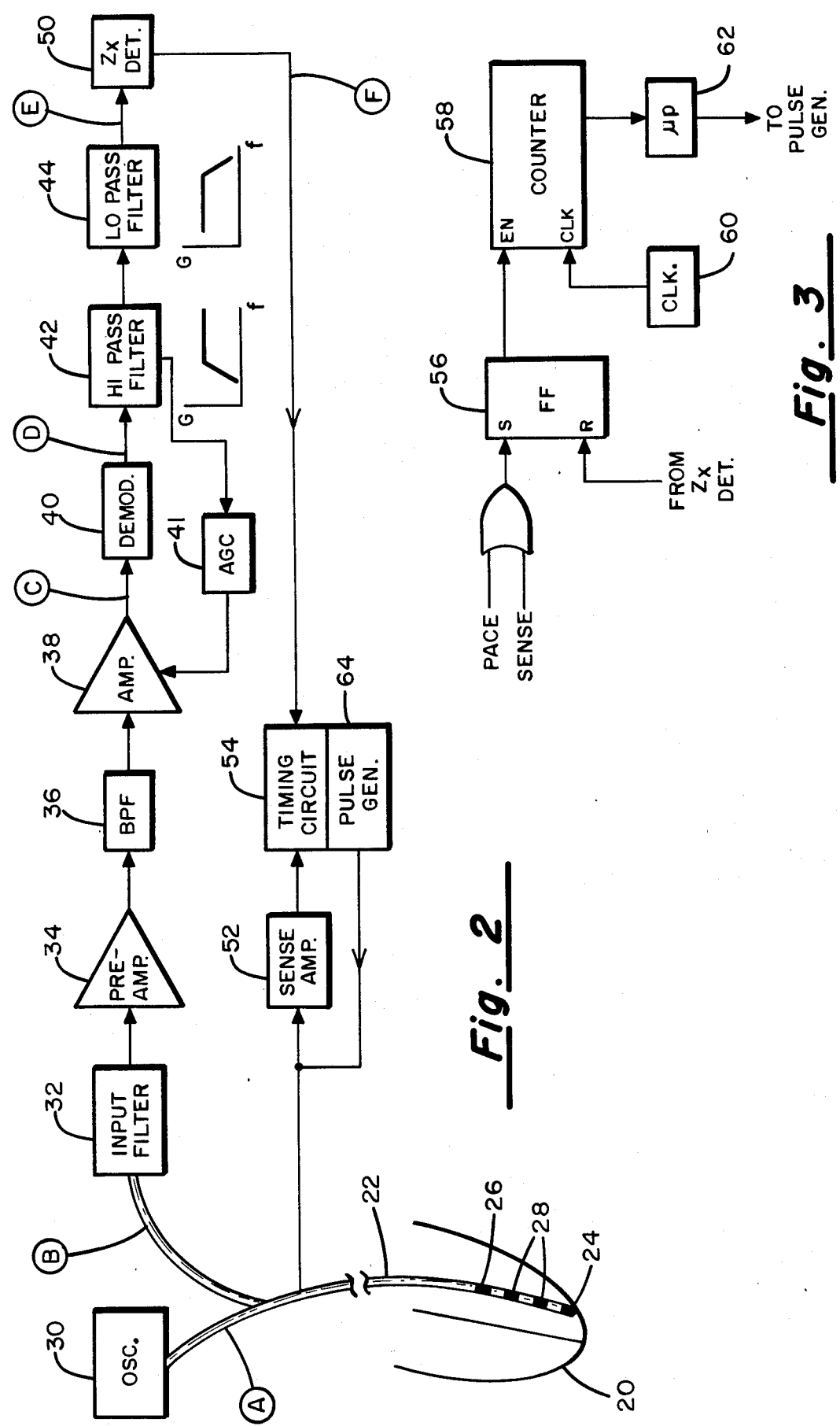

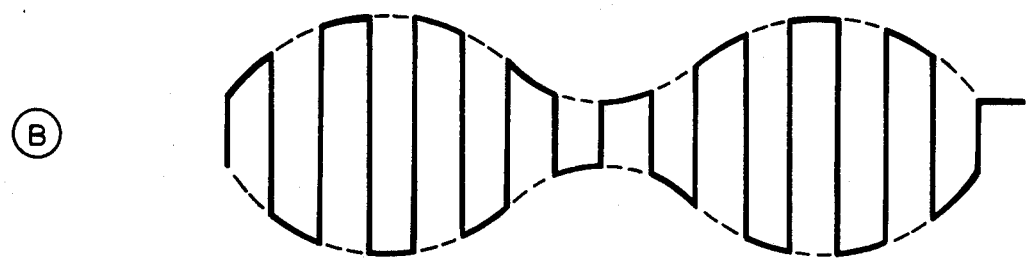
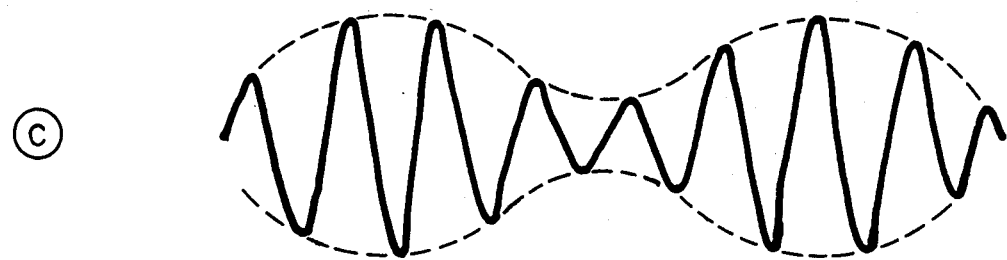
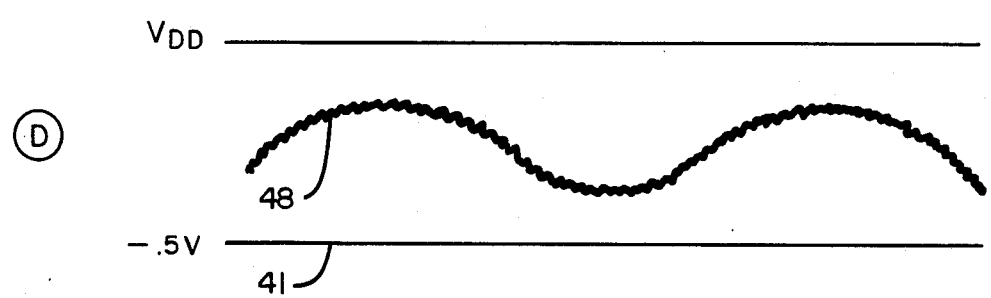
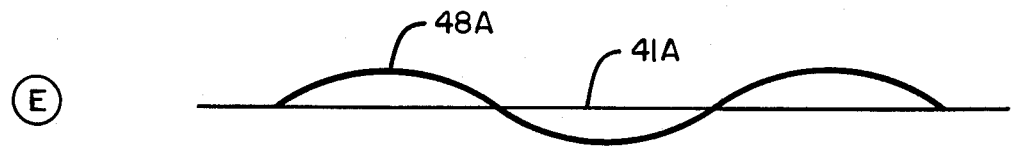
Fig. 4

PHYSIOLOGIC CONTROL OF PACEMAKER RATE USING PRE-EJECTION INTERVAL AS THE CONTROLLING PARAMETER

BACKGROUND OF THE INVENTION

I. Field of the Invention

This invention relates generally to cardiac pacing apparatus and more particularly to an improved physiologically adaptive cardiac pacemaker whose rate is controlled primarily as a function of the heart's pre-ejection interval but in a manner that greatly simplifies the actual implementation of the system.

II. Discussion of the Prior Art

It is now well recognized that a cardiac pacemaker which is adaptive to a patient's physiologic or metabolic demand offers advantages over fixed rate pacing. Persons skilled in the art have addressed or considered any number of different parameters which can be sensed and used to alter pacing rate. For example, the Alcidi U.S. Pat. No. 4,009,721 purports to use a pH sensor in cooperation with a demand pacemaker for causing the pacing rate to vary as a function of blood pH. Experience has shown, however, that it is difficult to find a pH probe which would remain stable over prolonged periods when implanted in the human body. The Knudson U.S. Pat. No. 4,313,412 monitors P-wave rate and varies the ventricular stimulating rate of the pacer as a function of changes in the P-wave rate. Again, the ability to reliably measure changes in P-wave rate over prolonged periods has proven difficult and furthermore, the P-wave rate is dependent somewhat on the ventricular rate and, as such, is not truly an independent variable in an adaptive system.

The Dahl U.S. Pat. No. 4,140,132 utilizes a motion sensor (accelerometer) to monitor the physical activity of the body and to alter the pacemaker's escape interval as a function of the motor activity. However, since this sensor is sensitive to any motion, it does not discriminate between externally generated sources of vibration, such as motor vehicles, and motion associated with exercise. Also, since body motion is not proportional to workload during exercise, the rate response based on a motion sensor is a non-physiological response tending to be very abrupt.

In the Salo et al application Ser. No. 362,903, filed Mar. 29, 1982, and entitled "BIOMEDICAL METHOD AND APPARATUS FOR CONTROLLING THE ADMINISTRATION OF THERAPY TO A PATIENT IN RESPONSE TO CHANGES IS PHYSIOLOGIC DEMAND", (now U.S. Pat. No. 4,686,987, issued Aug. 18, 1987) which is assigned to applicants' assignee, there is described a pacemaker in which a technique referred to as "impedance plethysmography" is used to measure the instantaneous stroke volume, on a beat-to-beat basis in the right ventricular chamber and changes in stroke volume either absolute or with respect to a reference is used to vary the pacer's escape interval. While effective rate control can be achieved using this approach, the stroke volume is somewhat dependent upon the subject's body position which can result in a pacing rate change when changing from an upright to a prone position.

The Rickards et al U.S. Pat. No. 4,527,568 describes a pacemaker which includes a means for varying the rate of the stimulus pulse generator by measuring the QT interval which, purportedly, varies in length with the physiological demands of the body. It has been shown that the QT interval of a normal healthy heart decreases as exercise or the body's demand for blood increases. It is also known, however, that the QT interval is pacing rate dependent and that the introduction of artificial stimulating pulses causes a decrease in the QT interval as well. This can result in a positive feedback situation wherein the combination of exercise and pacing results in an inordinately high acceleration.

In a patent application Ser. No. 770,205, filed Aug. 28, 1985, by Raul Chirife and entitled "CARDIAC PACEMAKER ADAPTIVE TO PHYSIOLOGICAL REQUIREMENTS", (U.S. Pat. No. 4,719,921) there is described a pacing system in which the left ventricular pre-ejection period is measured and converted to an electrical signal with such electrical signal being used to control the rate of a cardiac pacemaker. In the Chirife application, the pre-ejection period or PEP is defined as the period beginning with the QRS complex and ending with the onset of ventricular ejection. It is explained that the PEP varies predictably in response to the release of catecholamines into the blood and with direct sympathetic nerve activity when physiologic demands increase. The system of the Chirife invention suffers, however, from a practical standpoint in that it is unduly complex and difficult to implement with state-of-the-art apparatus. This is due primarily to the fact that the implementation requires a means for sensing the onset of left ventricular ejection. An effective sensor for this event is difficult to realize, given that it must be included in the implantable pacemaker housing or can.

The present invention provides a practical implementation of a rate controlled cardiac stimulator responsive to physiologic demand. Rather than attempting to measure the time between the occurrence of a paced or naturally occurring QRS complex and the onset of blood flow from the patient's left ventricle, and converting that to a voltage or digital value for adjusting the escape interval of a pacer, a multi-electrode lead located in the right ventricle is used to sense the instantaneous impedance within that ventricle as the chamber fills and empties of blood during the cardiac cycle. The resulting impedance versus time waveform is then electronically partitioned. The segment of the impedance waveform starting with a paced or sensed QRS complex (hereinafter referred to as the systole marker) and terminating at the first positive crossing of the impedance signal average following that systole marker or at some other easily defined point is the time interval of interest. This interval is found to be inversely proportional to contractility of the heart in that catecholamines or sympathetic stimulation results in a decrease of this time interval. Also, the interval in question is not subject to appreciable change due either to postural changes or changes in the ventricular pacing rate.

In that the systole marker is an easily detected event and conventional signal processing techniques, including a zerocrossing detector or other type of level detector, for operating on the impedance waveform are readily implementable with existing electronic componentry and compatible with the requirements for implantable devices (small size and low power drain), the system of the present invention proves practical and effective.

The system of the present invention also includes a means for accommodating long-term drift in the measurement of the physiologic variable. In particular, a baseline register is provided which holds a value against which the physiologic sensor output is compared in determining the ultimate pacing rate. A further multi-bit count register is incremented, decremented or left unaltered depending upon whether the sensor output exceeds, falls below or equals the baseline value, respectively, on each cardiac cycle. Subsequently, at fixed intervals greatly in excess of the time for a cardiac cycle, the aforementioned multi-bit count register is read to determine if it contains a positive, a negative or a zero value. If found to contain a positive value, the baseline value is incremented by one. If, however, the count register contains a negative value, the baseline will be decremented by one. If the count value should be zero, the contents of the baseline register is left unchanged. In this manner, over a prolonged period, the periodic adjustments to the baseline value will put the average physiological sensor output value into this register. Thus, rate changes due to long-term shifts in the output from the physiological sensor can be avoided.

OBJECTS

It is accordingly a principal object of the present invention to provide an improved implantable cardiac stimulating device where the stimulation rate is a function of physiologic demand.

Another object of the invention is to provide a rate responsive pacer in which the control parameter is based upon an intracardiac impedance measurement.

Yet another object of the invention is to provide a rate responsive pacer in which the rate adjustment is based upon a time interval defined by the systole marker and the immediately following positive crossing of the impedance signal with respect to its signal average value.

A still further object of the invention is to provide a rate responsive pacemaker whose escape interval is varied in accordance with an intracardiac impedance measurement which can be implemented with state-of-the-art electronic components.

A yet further object of the invention is to provide a rate responsive pacemaker in which long-term shifts in physiological sensor output are accommodated and do not adversely alter the pacing rate.

SUMMARY OF THE INVENTION

In carrying out the present invention, a cardiac pacemaker system includes a multi-electrode lead having a stimulating tip electrode and one or more proximately disposed surface electrodes which are appropriately positioned in the right ventricle and which are coupled by elongated conductors passing through the lead to an implanted rate responsive pacemaker. Contained within the pacemaker housing is a stimulating pulse generator having a timing circuit for controlling the escape interval of the pulse generator. Also enclosed within the pacemaker's can or housing is a drive oscillator for applying an alternating current potential either between a pair of the electrodes disposed in the right ventricle (bipolar) or at least one disposed in the apex of the right ventricle and another located elsewhere in the body (unipolar). A sensing circuit coupled to a pair of surface electrodes on the lead body or to one such surface electrode and to a remote (indifferent) electrode is also contained in the pacer can for detecting the modulation of the alternating current signal occasioned by the beating action of the patient's heart. The sensing means includes conventional signal processing apparatus including filtering, amplifying and demodulating circuitry for recovering the modulation envelope. The envelope signal comprises the impedance versus time waveform and after further filtering is applied to a zero-crossing detector whose baseline or reference is established by averaging the impedance waveform over a predetermined time interval. Further circuitry is provided for determining the time interval between the occurrence of a systole marker (R-wave) and the next succeeding crossing of the impedance signal through the averaged impedance value in a positive going direction. This interval is converted to an analog signal proportional to its duration or, alternatively, to a digital quantity representative of its duration, depending upon the nature of the timing circuit associated with the stimulation pulse generator of the pacemaker and is used to adjust the escape interval of that pacemaker.

DESCRIPTION OF THE DRAWINGS

The foregoing objects and advantages of the invention will become apparent to those skilled in the art from the following detailed description of a preferred embodiment, especially when considered in conjunction with the accompanying drawings in which:

FIG. 2 is a block diagram of the electrical circuitry used to develop the control parameter for adjusting the escape interval of a demand-type pacemaker;

FIG. 3 is a further block diagram showing position of the pacer's timing circuit;

FIG. 4 is a series of waveforms useful in understanding the operation of the circuitry of FIGS. 2 and 3.

DESCRIPTION OF THE PREFERRED EMBODIMENT

Figure 1:
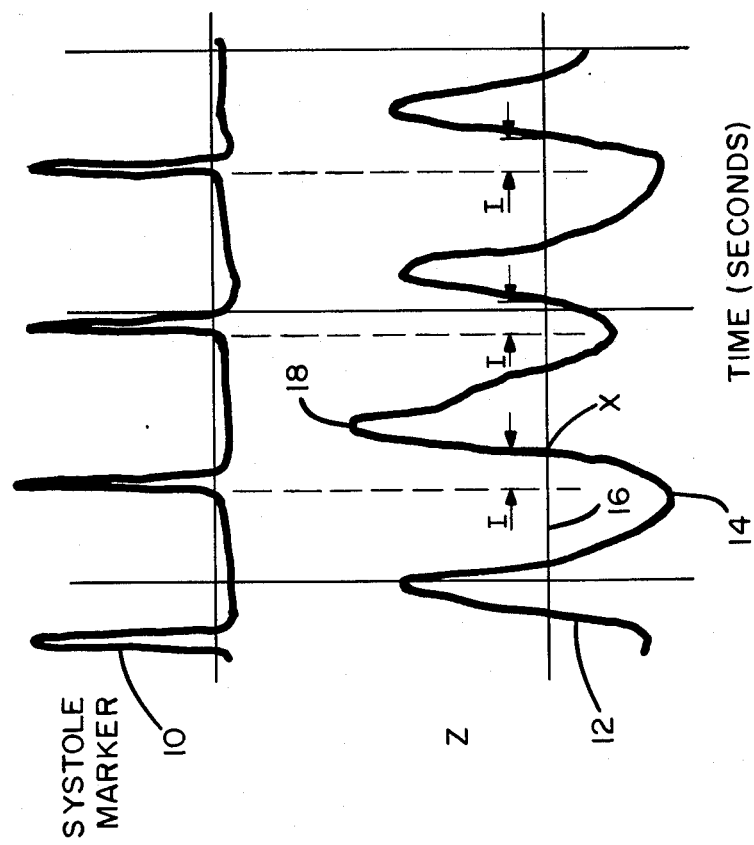
FIG. 1 illustrates waveforms of the impedance signal resulting from the influx and outflow of blood from the ventricular chamber aligned with a systolic marker.

Referring to FIG. 1, there is shown two waveforms superimposed on the same time scale, the upper waveform 10 representing the occurrence of systole events, typically a paced or a sensed QRS complex. Aligned in time beneath it is a waveform 12 showing the manner in which the intraventricular impedance, Z, changes with time due to the pumping action of the heart. During diastole of the atria, via the superior and the inferior venae cavae, coronary sinus, and other small vessels, blood enters and fills the right atrium and ventricle, which for the time may be thought of as a single chamber with its tricuspid valve open. The atrium contracts (atrial systole) and forces the blood through the valve into the ventricle, which has been passively filled and now becomes well distended by the extra blood supply. This corresponds to the minimum point 14 on the impedance curve 12. After a brief pause (0.1 second), rising muscle tension due to ventricular systole causes a rapid rise in the pressure of the ventricle. When this pressure exceeds that of the atrium, the cusps proximate each other close the valve. Chordae tendineae become taut and prevent the cusps from everting. As soon as the rapidly rising pressure in the ventricle exceeds the pressure in the pulmonary artery, the pulmonary semilunar valve is forced open and blood moves on into the pulmonary artery. This is reflected in the rising portion of the curve 12. Once the right ventricle empties to its residual capacity and just prior to the time that blood again begins to flow back in anticipation of the next ejection cycle, the impedance curve reaches its maximum value at 18. The semilunar valve then closes rapidly and the pulmonary artery delivers the blood to the lungs where oxidation takes place. The capillaries in the lungs unite to form veins which join to become the two pulmonary veins used to return the oxygenated blood to the heart, completing the pulmonary circulation cycle.

Because the positive going crossing of the impedance waveform 12 through the average impedance value 16 (as at X) following a systole marker is a readily detectable event, the interval "I" therebetween has been selected as the controlling variable for the stimulation pulse generator. It is to be noted that the interval "I" is greater than the pre-ejection period in that it includes a portion of the time in which the blood is being ejected from the right ventricle. Nevertheless, interval "I" is found to vary with exercise and with metabolic demand, but remains relatively independent of the pacing rate itself. Likewise, the interval "I" is found to be fairly independent of postural changes and, thus, the cardiac pacer constructed in accordance with the present invention does not exhibit any significant variation in escape interval depending upon whether the individual is standing or supine.

The manner in which the interval "I" is defined and converted to a pacemaker escape interval modifying signal will next be explained with the aid of FIGS. 2 and 3. Referring first to FIG. 2, the patient's heart is indicated schematically at 20 and disposed in the right ventricle thereof is a multiconductor pacing lead 22 having a stimulating tip electrode 24 at the distal end thereof, a drive electrode 26 disposed proximally thereof and a pair of intermediate surface electrodes 28 disposed therebetween. All of the electrodes 24 through 28 are shown as being disposed in the right ventricular chamber and are individually connected by conductors (not shown) contained within the lead body 22. However, as pointed out above, the proximal stimulating electrode 26 may be located elsewhere in the body and may, indeed, be the pacemaker "can" itself.

Conductors associated with the pacing and current drive tip electrode 24 and the drive electrode 26 are connected to a drive circuit 30 which may, for example, be a square wave oscillator producing pulses at a predetermined rate, e.g., 2.73 KHz, and of a fixed, extremely stable amplitude somewhere in the range of from 6 to 24 microamperes. This signal is illustrated as waveform A in FIG. 4.

As explained above, as blood flows in and out of the right ventricular chamber, impedance changes occur due to the changes in conductivity caused by the changes in blood volume in the right ventricle. This causes a voltage to be developed across the pair of impedance sensing electrodes 28 in accordance with Ohms law and this signal, labeled "B" in FIG. 4, is applied to an input filter 32. This signal to the filter may typically have a peak-to-peak amplitude of 120 microvolts and appears as an amplitude modulated signal with a square wave carrier. The input filter 32 serves to decouple the preamplifier 34 from the lead during and for a period in the range of from approximately 24 ms to 36 ms following a ventricular stimulating pulse, and the resulting signal from preamplifier stage 34 is fed through a band-pass filter 36 and a further gain controlled amplifier 38 to increase the amplitude of the signal and to effectively change the square wave carrier to a sine wave of basically the same frequency. The output from the amplifier 38 appears as waveform "C" in FIG. 4.

It is to be noted from the modulation envelope that when the heart is fully contracted and thus contains a minimum residual blood volume, the modulated voltage at "C" is a maximum and that when the heart again fills with blood prior to the next contraction, the modulated voltage signal is at its minimum.

The signal appearing at point "C" in FIG. 2 is next applied to a demodulator circuit 40 which is effective to remove the AC carrier signal so as to leave the time varying DC envelope at point "D" at the output of the demodulator. The demodulator 40 output is fed through a portion of the high pass filter 42 and from there through automatic gain control circuit 41 to the automatic gain control amplifier 38. The AGC circuit exhibits a time constant which is much greater than the period of the heart rate and is therefore effective to prevent long-term changes in the carrier amplitude due to blood impedance variations occasioned by changes in the blood electrolyte. Reference to waveform "D" in FIG. 4 shows a certain amount of noise superimposed upon the time varying DC envelope signal which, in turn, has a varying DC offset from the system reference voltage, typically (−0.5 volts). When this signal is applied to a hi-pass filter 42 followed by a lo-pass filter 44, these two filtering operations are effective to first eliminate the DC offset from the system reference and to remove the noise component.

The output from the lo-pass filter 44 is next applied to a ZX (zero crossing) detector 50 which preferably comprises a comparator circuit having hysteresis such that when the signal 48A applied to the ZX detector 50 exceeds the system reference voltage 41A in a positive direction, the comparator output shifts from a low condition to a high condition. See waveforms E and F in FIG. 4. It is also contemplated that some other percentage of the peak-to-peak impedance signal, other than 50% (i.e., zero-crossing), may be the threshold for defining the terminus for the interval "I" (FIG. 1). In this regard, a threshold level in the range of from 15% to 50% of the peak-to-peak impedance signal is deemed to produce effective results.

Referring to FIG. 3, the manner in which the escape interval controlling signal is developed will next be explained.

Conventional demand-type pacemakers include a sense amplifier as at 52 which detects either paced or sensed R-waves picked up by the tip electrode 24 on the implanted lead. The output from the sense amplifier 52 is applied to the pacer's timing circuit 54, which may include a set-reset flip-flop 56 whose output is connected to the enable (En) input of a multistage binary counter 58. When enabled, the counter 58 counts the number of regularly occurring relatively high frequency clock signals emanating from a clock source 60. When the output from the ZX detect circuit 50 goes high, the flip-flop 56 is reset and the enable is removed from the counter 58. Thus, the number of clock pulses accumulated or captured in the counter 58 between the time of occurrence of the paced or sensed R-wave event and the occurrence of the next subsequent crossing of the impedance waveform through the predetermined reference level is a value directly related to the desired time interval in question. The count value in question may then be applied to a microprocessor 62 controlling the operation of the stimulation pulse generator 64 (FIG. 2). Typically, the microprocessor will keep a running average of the beat-by-beat value in counter 58. By using approximately 2 to 16 values in the running average, beat-to-beat rate variations are minimized. As will be further explained hereinbelow, the microprocessor 62 is programmed to compare the running average sensor value with a baseline value which represents the expected value at rest. If the average developed turns out to be less than the baseline value, the microprocessor 62 accesses a ROM memory (not shown) containing values defining the extent to which the escape interval of the pacer is to be shortened as a function of the difference between the average value developed and the current baseline value maintained in an internal register of the microprocessor 62. This decrement value is then subtracted from the value defining the then current escape interval, resulting in a command to the pulse generator 64 to issue a stimulation pulse a predetermined time sooner than the prior current value would have dictated. If, on the other hand, it turns out that the average sensor value developed is greater than the baseline value, no foreshortening of the pulse generator's escape interval takes place.

At any given instant, the current pacing rate will be proportional to the difference between the averaged sensor output and the baseline value. Thus, if the two values are equal, the pacing rate will be equal to the programmed base rate. A baseline tracking mechanism is further provided to allow the baseline value to slowly track long-term drifts in the value of the sensor output.

Figure 5:
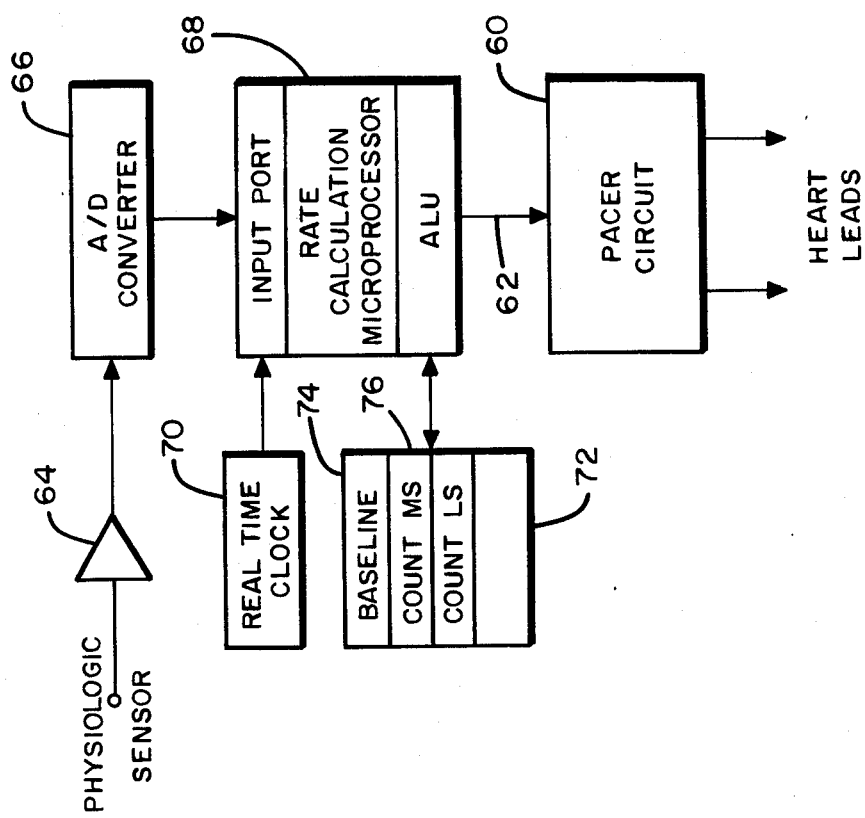
FIG. 5 is a block diagram of the circuitry employed to compensate for any long-term drift in the characteristics of the physiological sensor used in a rate responsive pacemaker.

The circuitry for implementing the baseline tracking feature is shown in FIG. 5. This circuitry is not only applicable to the physiologic sensor used in the embodiment of FIGS. 2 and 3 but may be used in any rate responsive pacemaker whose physiologic sensor may drift with time. The circuit of FIG. 5 provides a means for tracking long term changes in the sensor's baseline value. In accordance with the implementation of FIG. 5, the pacemaker circuit is identified by numeral 60 and it includes a control port 62 which allows control of the escape interval thereof in response to a monitored physiological variable. The input from the physiological sensor which, in the embodiment of FIG. 3, may be the output from the lo-pass filter 44, is applied, via an impedance matching amplifier 64, to an analog-to-digital converter 66 configured to deliver a single digital value of the sensor output for each cardiac cycle. The output from the analog-to-digital converter 66 is applied to a rate calculation circuit 68 which takes this value and calculates the stimulation rate for the pacer on a cycle-by-cycle basis. A real-time clock 70 is provided which is arranged to interrupt the rate calculation circuit 68 at fixed intervals, typically in the range of from one-half minute to several minutes.

Also coupled to the rate calculation circuit 68 is a register bank 72 capable of storing a plurality of values. Specifically, the register bank 72 may be configured to store three 8-bit words, one an 8-bit "baseline" value and the other two 8-bit count values which, when combined, form a 16-bit word. The upper 8-bits of the count value in register 76 comprise the most significant byte of the 16-bit word while the lower count register 78 stores the least significant 8-bit byte.

The "baseline" register 74 holds the value against which the digitized sensor input is compared to determine the appropriate rate adjustment. Initially, register 74 is set to the sensor value existing when the patient is at rest. The 16-bit count register 76-78 is initially set to zero. On each cardiac cycle, the new sensor running average value will be compared to the baseline value stored in register 74. If the digitized sensor value is above the baseline value, then the count register 76-78 is incremented by one. If the sensor value is below the baseline, the count is decremented by one. If equal, the count is left unchanged. Computations in the rate calculation circuit 68 are done on a 2's complement basis such that the most significant bit of the upper count register 76 constitutes a sign bit.

At periodic intervals determined by the real-time clock 70, the contents of the count register is read to determine if it is positive, negative or zero. If the count value is positive, the baseline value is incremented by one. If negative, the baseline value is decremented by one. If the count value is zero, the baseline value is left unchanged. Following that, the count register is cleared and the process is reinitiated.

It can be seen, then, that over time, the periodic adjustments to the "baseline" value will put the average value of the sensor output into the baseline register. In this manner, rate changes due to long-term shifts in the sensor value are avoided.

Those skilled in the art will recognize that the number of bits employed and the method of calculation of the baseline and count values can be changed without substantially altering the result. The pacer control and rate calculation circuits may also be combined, which is perhaps preferred, when the pacer circuit, itself, is microprocessor-based. The use of the digital approach to implement baseline tracking reduces the components required and also improves the overall accuracy. Furthermore, the use of the real-time clock 70 to establish the adjustment interval allows the time constant of the baseline tracking system to be programmable. Nonetheless, those skilled in the art will be in a position to implement the baseline tracking feature using analog components.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. In a cardiac pacer of the type including pulse generating means for applying tissue stimulating pulses to the heart in the absence of naturally occurring contractions during a predetermined escape interval and adjustable timing means coupled to said pulse generating means for altering the length of said escape interval in accordance with a sensed physiologic parameter, the improvement comprising:
   (a) intracardiac impedance detecting means for continuously generating an impedance variations with time signal relating to such variations in one ventricular chamber of the heart due to the inflow and outflow of blood therefrom;
   (b) means for generating a systole marker event signal;
   (c) means responsive to said detecting means for measuring the time interval elapsing between the occurrence of said systole marker event signal and the next succeeding crossing of a predetermined reference by said impedance variation with time signal;

(d) means for converting said measured time interval to an escape interval control value; and (e) means for applying said escape interval control value to said adjustable timing means.

2. The cardiac pacer as in claim 1 wherein said impedance detecting means comprises:

(a) means for injecting an alternating current carrier signal between two spaced locations, at least one of which is disposed within said one ventricular chamber;

(b) electrode means disposed proximate said spaced locations for sensing the voltage signal variations resulting from said injected carrier signal and the rhythmic changes in blood volume in said one ventricular chamber due to the beating action thereof, said voltage signal variations being an amplitude modulated carrier signal;

(c) signal processing means including demodulator means coupled to said electrode means for recovering the modulation voltage envelope from said amplitude modulated carrier signal.

3. The cardiac pacer as in claim 2 wherein said means responsive to said detecting means comprises:

(a) means for sensing the occurrence of said systole marker event signal;

(b) comparator means, including means for establishing a reference level, and being coupled to receive said modulation voltage envelope for signaling when the modulation voltage exceeds said reference level; and (c) timer means responsive to said occurrence of said systole marker event signal for starting said timer means and to the output of said comparator means for stopping said timer means.

4. In a cardiac pacer of the type including pulse generating means for applying tissue stimulating pulses to the heart in the absence of naturally occurring R-wave activity taking place during a predetermined escape interval, physiologic sensing means for sensing a predetermined physiologic parameter within the body, and means responsive to said physiologic sensor means for altering the length of said escape interval as a function of the body's physiologic demand, the improvement comprising:

(a) analog-to-digital converter means for receiving a signal proportional to the measured physiologic parameter for converting said signal to a digital quantity;

(b) program controlled microprocessor means coupled to said analog-to-digital converter means for receiving said digital quantity;

(c) a plurality of storage registers for storing a baseline value and a count value, said storage registers being operatively coupled to said microprocessor means;

(d) arithmetic means in said microprocessor means operative on each cardiac cycle for adjusting said escape interval of said pulse generating means in accordance with the difference between said baseline value and said digital quantity contained in one of said plurality of storage registers, said microprocessor means being programmed to control said arithmetic means to increment, decrement or leave unaltered said count value stored in another of said plurality of registers depending upon whether said digital quantity is less than, greater than, or equal to the baseline value during that cardiac cycle, respectively; and (e) means operated by said program controlled microprocessor means, repetitively at time periods greatly in excess of the time for each cardiac cycle, for examining said count value stored in said another of said plurality of registers and altering said baseline value depending on the algebraic sign of said count value.

5. In a cardiac pacer of the type including pulse generating means for applying tissue stimulating pulses to the heart in the absence of naturally occurring contractions during a predetermined escape interval and adjustable timing means coupled to said pulse means for altering the length of said escape interval in accordance with a sensed physiologic parameter, the improvement comprising:

(a) intracardiac impedance detecting means for continuously generating an impedance variation with time signal relating to such variations in one ventricular chamber of the heart due to the inflow and outflow of blood therefrom;

(b) means for generating a systole marker event signal;

(c) means for sensing the occurrence of said systole marker event signal;

(d) comparator means, including means for establishing a reference level and being coupled to receive said impedance variation with time signal for signaling when said impedance variation with time signal exceeds said reference level;

(e) timer means having means responsive to the occurrence of said systole marker event signal for initiating a timing interval and to the output of said comparator means for ending said timing interval;

(f) means for converting said timing interval to a pacer escape interval control value; and (g) means for applying said escape interval control value to said adjustable timing means.

6. The cardiac pacer as in claim 5 wherein said reference level falls in the range of from fifteen percent and fifty percent of the average peak-to-peak value of said impedance variation with time signal.

7. The cardiac pacer as in claim 5 wherein said timer means comprises:

(a) a source of regularly occurring clock pulses of a predetermined, fixed repetition rate;

(b) counting means coupled to receive said clock pulses for counting same only when said counting means is enabled;

(c) means responsive to said systole marker event signal for enabling said counting means; and (d) means for disabling said counting means upon the occurence of said output from said comparator means.

8. The cardiac pacer as in claim 7 wherein said means for applying said escape internal control value to said adjustable timing means of said packer comprises:

(a) memory means for storing a plurality of control values at addreeable locations therein;

(b) means responsive to the contents of said counting means for generating addresses for said memory means; and (c) means for algebraically adding said control values to the current value in said adjustable timing means defining the length of said escape interval.

* * * * *

UNITED STATES PATENT AND TRADEMARK OFFICE
CERTIFICATE OF CORRECTION

PATENT NO. : 4,773,401

DATED : September 27, 1988

INVENTOR(S) : Brian P. Citak, et al

It is certified that error appears in the above-identified patent and that said Letters Patent is hereby corrected as shown below:

Column 10, line 59, delete "packer" and put instead -- pacer --.

Signed and Sealed this

Tenth Day of January, 1989

Attest:

DONALD J. QUIGG

Attesting Officer

Commissioner of Patents and Trademarks